(12) United States Patent
Waters (10) Patent No.: US 8,162,836 B2
(45) Date of Patent: Apr. 24, 2012

(54) SYSTEM AND METHOD FOR CHARACTERIZING TISSUE BASED UPON SPLIT SPECTRUM ANALYSIS OF BACKSCATTERED ULTRASOUND

(75) Inventor: Kendall Rand Waters, Lakewood, OH (US)

(73) Assignee: Volcano Corporation, Rancho Cordova, CA (US)

( * ) Notice: Subject to any disclaimer, the term of this patent is extended or adjusted under 35 U.S.C. 154(b) by 1338 days.

(21) Appl. No.: 11/767,807

(22) Filed: Jun. 25, 2007

(65) Prior Publication Data

US 2007/0299343 A1   Dec. 27, 2007

Related U.S. Application Data

(60) Provisional application No. 60/816,286, filed on Jun. 23, 2006.

(51) Int. Cl.
*A61B 8/00*   (2006.01)
(52) U.S. Cl. ......... 600/443; 600/437; 600/463; 600/467
(58) Field of Classification Search ................. None
See application file for complete search history.

(56) References Cited

U.S. PATENT DOCUMENTS

| | | | |
|---|---|---|---|
| 4,873,984 A | 10/1989 | Hunt et al. | |
| 5,417,215 A | 5/1995 | Evans et al. | |
| 6,200,268 B1 | 3/2001 | Vince et al. | |
| 2005/0277835 A1* | 12/2005 | Angelsen et al. | 600/437 |

OTHER PUBLICATIONS

Kawasaki et al., "In Vivo Quantitative Tissue Characterization of Human Coronary Arterial Plaques by Use of Integrated Backscatter Intravascular Ultrasound and Comparison With Angioscopic Findings," *Circulation*, 105(21), pp. 2487-2492, May 28, 2002.
Urbani et al., "In Vivo Radiofrequenty-Based Ultrasonic Tissue Characterization of the Atherosclerotic Plaque," From CNR, Institute of Clinical Physiology, Pisa (M.P.U., E.P., A.M., M.P., G. Pelosi, L.L.), and the Institute of Neurosurgery, University of Pisa, (G. Parenti, L.F.) Italy. pp. 1507-1512, May 20, 1993.
Landini et al., "Evaluation of Frequency Dependence of Backscatter Coefficient in Normal and Atherosclerotic Aortic Walls"; C,N.R. Institute of Clinical Physiology, University of Pisa, Pisa, Italy 1986, vol. 12, n°5, pp. 397-401 (24 ref.).

\* cited by examiner

*Primary Examiner* — Unsu Jung
*Assistant Examiner* — Bo J Peng
(74) *Attorney, Agent, or Firm* — Haynes and Boone, LLP (57) ABSTRACT

A system and method are disclosed that facilitate characterizing vascular plaque tissue based upon spectral analysis of intravascular ultrasound echo signal segments. In particular, split spectrum analysis of an integrated backscatter parameter introduces a spectral resolution component to parameterization of received intravascular ultrasound echo signal segments. The resulting parameter values for each of multiple bands within a larger frequency band supported by an ultrasound system are applied to plaque tissue characterization criteria to render a plaque tissue characterization corresponding to the corresponding ultrasound echo signal segments.

20 Claims, 6 Drawing Sheets

SYSTEM AND METHOD FOR CHARACTERIZING TISSUE BASED UPON SPLIT SPECTRUM ANALYSIS OF BACKSCATTERED ULTRASOUND

CROSS-REFERENCE TO RELATED APPLICATION

This application claims priority of Waters U.S. provisional application Ser. No. 60/816,286 filed on Jun. 23, 2006, entitled "Split Spectrum Analysis for Intravascular Ultrasound Tissue Classification," the contents of which are expressly incorporated herein by reference in their entirety including the contents and teachings of any references contained therein.

FIELD OF THE INVENTION

The present invention generally relates to the field of imaging systems, and more particularly to intravascular ultrasound imaging systems and methods for diagnosing vascular disease.

BACKGROUND

The development of new medical technologies has provided an increasing number of options available to doctors for the diagnosis and treatment of cardiovascular diseases. The availability of such equipment has improved the ability of doctors and surgeons to detect and treat cardiovascular disease. Intravascular imaging technologies have enabled doctors to create and view a variety of images generated by a sensor inserted within a vasculature. Such images complement traditional radiological imaging techniques such as angiography by providing images of the tissue within vessel walls rather than showing a two dimensional lumen image.

Intravascular ultrasound (IVUS) analysis finds particular application to a system and method for quantitative component identification within a vascular object including characterization of tissue. It should be appreciated that while the exemplary embodiment is described in terms of an ultrasonic device, or more particularly the use of IVUS data (or a transformation thereof) to characterize a vascular object, the present invention is not so limited. Thus, for example, using backscattered data (or a transformation thereof) based on ultrasound waves or even electromagnetic radiation (e.g., light waves in non-visible ranges) to characterize any tissue type or composition is within the spirit and scope of the present invention.

Imaging portions of a patient's body provides a useful tool in various areas of medical practice for determining the best type and course of treatment. Imaging of the coronary vessels of a patient by techniques involving insertion of a catheter-mounted probe (e.g., an ultrasound transducer array) can provide physicians with valuable information. For example, the image data indicates the extent of a stenosis in a patient, reveals progression of disease, and helps determine whether procedures such as angioplasty or atherectomy are indicated or whether more invasive procedures are warranted.

In an ultrasound imaging system, an ultrasonic transducer probe is attached to a distal end of a catheter that is carefully maneuvered through a patient's body to a point of interest such as within a coronary artery. The transducer probe in known systems comprises a single piezoelectric crystal element that is mechanically scanned or rotated back and forth to cover a sector over a selected angular range. Acoustic signals are transmitted and echoes (or backscatter) from these acoustic signals are received. The backscatter data is used to identify the type or density of a scanned tissue. As the probe is swept through the sector, many acoustic lines (emanating from the probe) are processed to build up a sector-shaped cross-section image of tissue within the patient. After the data is collected, an image of the blood vessel (i.e., an IVUS image) is reconstructed using well-known techniques. This image is then visually analyzed by a cardiologist to assess the vessel components and plaque content. Other known systems acquire ultrasound echo data using a probe comprising an array of transducer elements.

In a particular application of IVUS imaging, ultrasound data is used to characterize tissue within a vasculature and produce images graphically depicting the content of the tissue making up imaged portions of a vessel. Examples of such imaging techniques for performing spectral analysis on ultrasound echoes to render a color-coded tissue map are presented in Nair et al. U.S. Pat. No. 7,074,188 entitled "System and Method of Characterizing Vascular Tissue" and Vince et al. U.S. Pat. No. 6,200,268 entitled "Vascular Plaque Characterization", the contents of which are incorporated herein by reference in their entirety, including any references contained therein. Such systems analyze response characteristics of ultrasound backscatter (reflected sound wave) data to identify a variety of tissue types found in partially occluded vessels including: fibrous tissue (FT), fibro-fatty (FF), necrotic core (NC), and dense calcium (DC).

When characterizing the response of tissue that has been subjected to ultrasound waves, parameter values are considered at a data point in an imaged field. Based upon response characteristics (e.g., power spectra) of known tissue types, tissue at the data point is assigned to a particular tissue type (e.g. necrotic core). Known systems utilize an integrated backscatter parameter that represents a power response over a frequency band. The integrated backscatter parameter generally represents a measure of total reflected ultrasound power at a particular point within a vasculature over a specified frequency band.

SUMMARY OF THE INVENTION

In accordance with the present invention a method and a supporting system operating according to computer-executable instructions characterize tissue components of plaque within blood vessels. For a given ultrasound echo signal segment, an integrated ultrasound backscatter parameter value is determined for each of at least two differing frequency ranges (bands). The at least two integrated backscatter parameter values are thereafter processed in combination to characterize a volume of tissue to which the ultrasound echo signal segment corresponds.

More particularly, a method for characterizing plaque tissue in accordance with received intravascular ultrasound echo segments is described herein. The method includes collecting analog ultrasound echo signals from a region of interest in a portion of an imaged body. Such region of interest is, for example, a blood vessel. Thereafter, the system computes, from RF-domain ultrasound echo signal segment data derived from the analog ultrasound echo signals, spectrally resolved information over an operating frequency range. The spectrally resolved information includes: a power spectrum rendered by performing spectral analysis, and a system transfer function.

Thereafter, the system determines, in each of at least a first sub-band and a second sub-band within the operating frequency range, an integrated backscatter parameter from the power spectrum and system transfer function. The frequency ranges are, by way of example adjacent, but not overlapping. However, in other embodiments the first and second sub-bands have overlapping ranges or band gaps between them.

The system thereafter compares integrated backscatter values from at least the first sub-band and the second sub-band to obtain at least one integrated backscatter comparison parameter value. The comparison parameter value is for example, is based upon signed difference value. Alternatively, the comparison value is based upon a ratio of the first and second sub-band integrated backscatter values.

Thereafter, the system applies the at least one integrated backscatter comparison parameter value to at least one tissue characterization criterion for rendering a plaque tissue characterization.

BRIEF DESCRIPTION OF THE DRAWINGS

While the claims set forth the features of the present invention with particularity, the invention, together with its objects and advantages, may be best understood from the following detailed description taken in conjunction with the accompanying drawing of which:

DETAILED DESCRIPTION OF THE DRAWINGS

Figure 4:
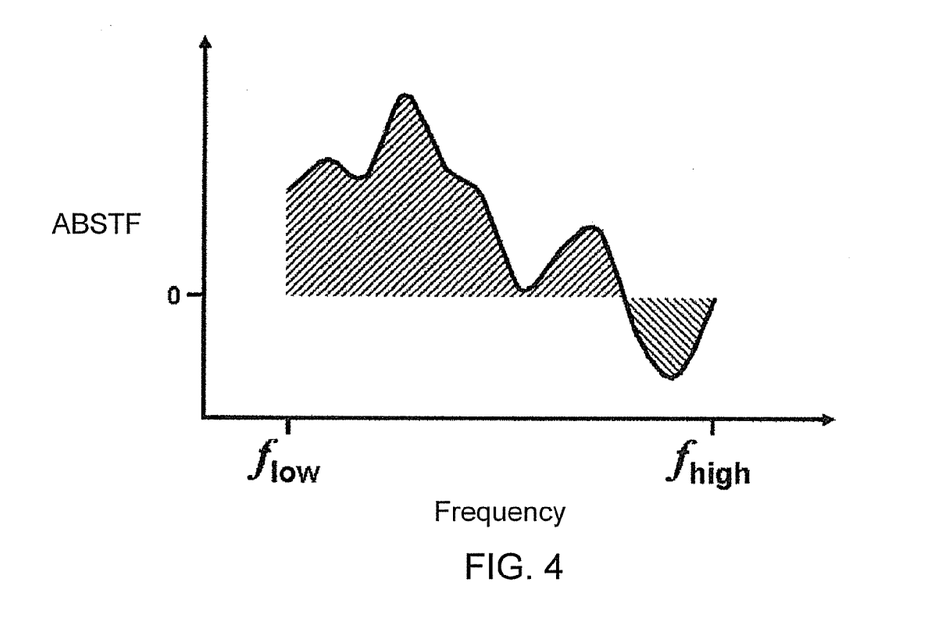
FIG. 4 is an exemplary graphical depiction of an apparent backscatter transfer function (ABSTF) for an echo signal segment.

Characterizing various types of tissue that make up plaque found within blood vessels facilitates classifying the larger plaque structures in order to diagnose and treat vascular disease. In the context of the disclosed system, a parameterized property of interest is a backscatter power coefficient that is indicative of how strongly a microscopic volume of tissue scatters ultrasound back to an ultrasound source. In accordance with exemplary embodiments system-dependent spectral characteristics of the IVUS system 100 are deconvolved from the backscatter power from tissue using a blind deconvolution operation. Deconvolution is an engineering discipline that improves the fidelity in electronic signals by removing (i.e., deconvolving) features of the signal that depend only on the imaging or measurement system (e.g., IVUS system). Blind deconvolution is a process in which the system-dependent characteristics are not a priori known. Such a process is described, by way of example, in Jirik and Taxt, EEE Ultrasonics, Ferroelectrics, and Frequency Control, Vol. 53, No. 8, 2006, pp. 1440-1448. The resulting normalized backscatter power is referred to as the apparent backscatter transfer function (ABSTF). FIG. 4 graphically depicts an example of an ABSTF (in logarithmic dB scale) derived from the backscatter power coefficient for an ultrasound echo signal segment. The ABSTF approximates the backscatter power coefficient. The ABSTF is depicted over a measured frequency band corresponding to, for example, the operating frequency spectrum of a system. The area under the ABSTF curve (representative of an echo signal segment's total backscatter power over a given frequency range) normalized (e.g., divided) by the bandwidth ($f_{high}-f_{low}$) to account for unequal and/or variable bandwidths, is referred to herein as the integrated backscatter (IB). The IB thus represents the average of the ABSTF curve over a specified bandwidth.

The polarity of the signal value is maintained during the IB calculation. Thus, the portions of the graph above the "0" amplitude level indicate a positive contribution to the IB value. The portions of the graph below the "0" amplitude level indicate a negative contribution to the IB for a backscatter signal. The IB provides a measure of the frequency-averaged backscatter power of a particular tissue volume over a designated frequency band from $f_{low}$ to $f_{high}$.

Figure 5:
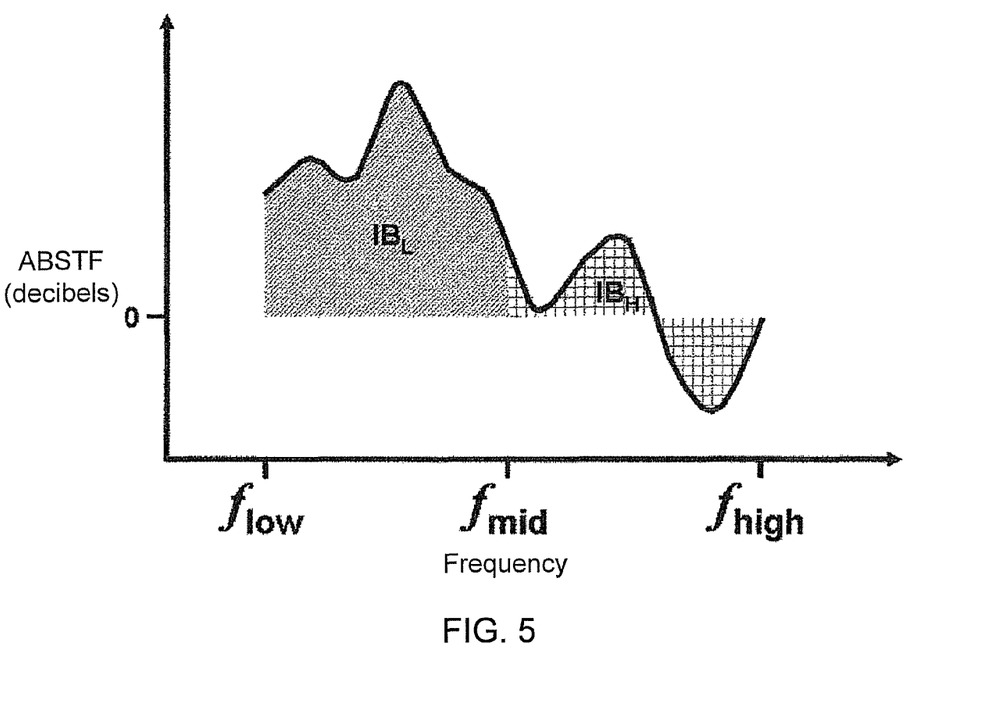
FIG. 5 is an exemplary graphical depiction of an ABSTF for an echo signal segment that has been split into low and high frequency bands for calculating low and high IB parameter values.

Turning to FIG. 5, the disclosed system and method for characterizing plaque tissue in blood vessels improve the spectral resolution of IB-based characterization schemes by splitting the operating frequency range of an IVUS system into at least two bands. In the exemplary embodiment the operating range ($f_{low}$ to $f_{high}$) is split into a low band ($f_{low}$ to $f_{mid}$) and a high band ($f_{mid}$ to $f_{high}$). Alternatively the operating frequency range is split into even more sub-bands. Furthermore, while the illustrative example designates two, non-overlapping, adjacent bands, alternative embodiments utilize overlapping bands as well as ones with gaps between one or more bands of interest.

Based upon the split frequency range, an $IB_{low}$ parameter value and an $IB_{high}$ parameter value are calculated from the ABSTF in the respective low and high sub-bands of the full operating band. Yet other examples of potentially useful IB-based parameters providing enhanced spectral resolution for characterizing plaque tissue (e.g., by applying to a tissue characterization decision tree) include: (1) a difference between the $IB_{low}$ and $IB_{high}$ values, and (2) a ratio of $IB_{low}$ to $IB_{high}$.

Furthermore, other embodiments of the present invention utilize the split spectrum of the ABSTF to render other spectrally resolved parameterized data. Examples include slope and intercept parameters from a linear regression of the ABSTF within each sub-band.

The spectrally resolved parametric data values from at least two distinct bands within a larger operating frequency range of an ultrasound system are thereafter applied to characterization criteria to render a characterization for the tissue corresponding to the intravascular ultrasound signal segment. Experimentation has confirmed that splitting a larger available frequency band into two or more sub-bands for purposes of rendering a set of IB parameters from a same intravascular ultrasound echo segment, facilitates identifying particular types of tissue (e.g., fibro-fatty and necrotic core) within plaque deposits in blood vessels.

It is furthermore noted that both analog and/or digital processing methods are potentially used to define the sub-bands in a split-spectrum analysis that renders parameter values representing the spectral power response of intravascular ultrasound echo signal segments in specified sub-bands (to render the IB parameter values for each spectral band). Furthermore, the various system implementations utilize a variety of components to analyze and render IB parameters, including: analog circuitry and digital circuitry as well as hardware/firmware/software and combinations thereof.

An exemplary IVUS (intravascular ultrasound) system includes an ultrasonic probe device mounted upon a flexible elongate member for insertion into vasculature. The system furthermore includes a computing device comprising memory for storing computer executable instructions associated with rendering a set of IB parameter values for a given ultrasound echo signal segment corresponding to particular sub-bands of a larger band associated with an ultrasound system. Additional computer executable instructions stored on the computing device apply the set of IB parameter values to plaque tissue characterization criteria. In the detailed description of the exemplary embodiment that follows, like element numerals are used to describe like elements illustrated in one or more figures.

Figure 1:
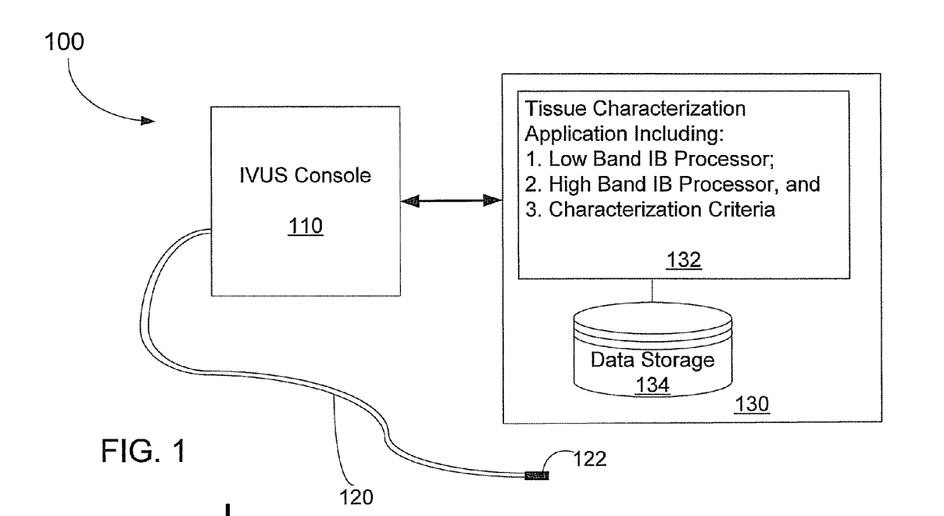
FIG. 1 illustrates a tissue-characterization system suitable for carrying out a tissue/plaque characterization scheme including an integrated backscatter parameter generator that generates, for a given ultrasound echo segment, at least a first and second integrated backscatter parameter value over differing sub-bands of a larger frequency band.

Turning to FIG. 1, a vascular plaque tissue characterization system 100 is schematically depicted. An intravascular ultrasound console 110 is communicatively coupled to an IVUS catheter 120. The IVUS catheter 120 comprises a distally mounted ultrasound transducer probe 122 that acquires backscatter data (e.g., IVUS data) from a blood vessel. In accordance with known IVUS catheters, the catheter 120 is maneuvered through a patient's body (e.g., via a femoral artery) to a point of interest. The transducer probe 122 is then controlled, via the console 110 to emit ultrasound pulses and thereafter receive echoes or backscattered signals reflected from vascular tissue/plaque and blood. Because different types and densities of tissue absorb and reflect (backscatter) the ultrasound pulse differently, the reflected ultrasound echo data (i.e., IVUS data) signals transmitted back to the console 110 by the IVUS catheter 120, are converted by characterization software into images of vascular objects. It should be appreciated that the IVUS console 110 depicted herein is not limited to any particular type of IVUS console, and includes all ultrasonic devices known to those skilled in the art (e.g., In-Vision Gold and s5™ systems of Volcano Corporation). It should further be appreciated that the IVUS catheter 120 depicted herein is not limited to any particular type of catheter, and includes all ultrasonic catheters known to those skilled in the art. Thus, for example, a catheter having a single transducer (e.g., adapted for rotation) or an array of transducers (e.g., circumferentially positioned around the catheter) is within the spirit and scope of the present invention.

Known imaging applications executed on an IVUS console (e.g. console 110) or a communicatively coupled computing device (e.g., computing device 130), render a variety of image types from received echo information. A first type of imaging application converts ultrasound echo signal data into gray scale images reflecting the relative strength of the echo signal returned by the objects within the transducer probe 120's field of view. In such imaging applications, the relatively light and dark regions indicate different tissue types and/or densities.

Other imaging applications, such as a tissue characterization application 132 executed on the computing device 130 communicatively coupled to console 110, renders tissue type information based upon the spectral (e.g., frequency and power) characteristics of the echo information received by the console 110 from the catheter 120. In accordance with an illustrative embodiment, IB parameter values are rendered from spectral analysis of the ultrasound echo information. In particular, IB parameter values are rendered for each of multiple sub-bands of an operating frequency band of the system 100 by corresponding IB processors (e.g., Low Band IB Processor and High Band IB Processor). The Low and High Band IB processors are identified separately in FIG. 1. However, in an exemplary embodiment, a single dynamically configurable IB processor renders IB parameter values on the fly from one of multiple selectable frequency sub-bands.

Figure 2:
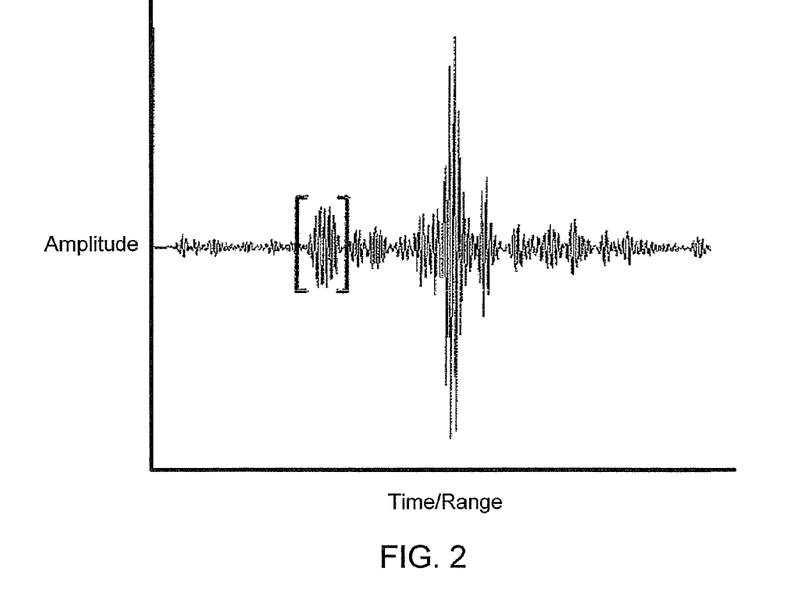
FIG. 2 illustrates an exemplary graphical depiction of a received ultrasound echo signal's amplitude over a period of time.
Figure 3:
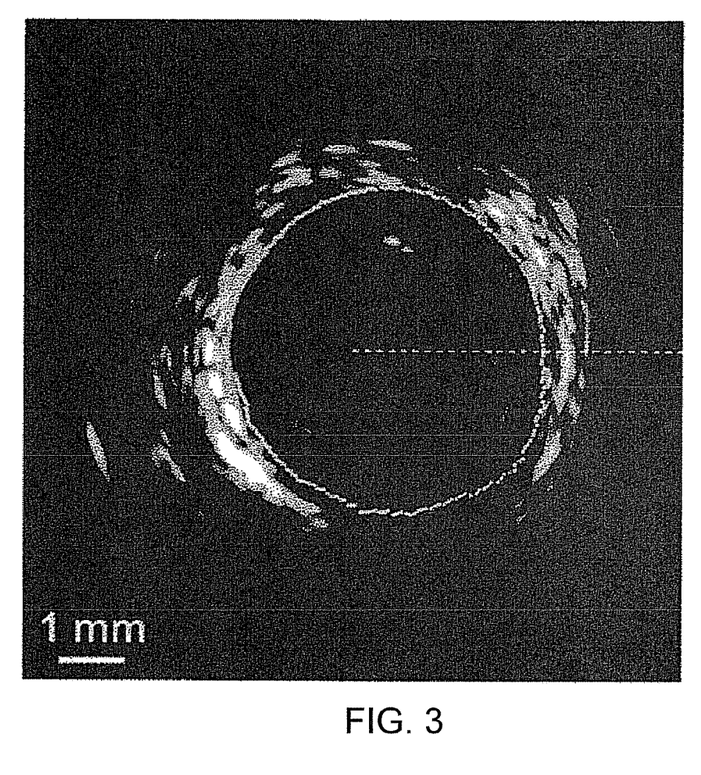
FIG. 3 is an exemplary grayscale ultrasound image of a vessel's cross-section.

Furthermore ultrasound power spectra from which IB parameter values are calculated in any of many potential ways. In illustrative examples, described further herein below, the ultrasound power spectrum (dividable into at least two sub-bands corresponding to Low and High Band IB parameters) is calculated by applying either Fourier or autoregressive modeling techniques to an ultrasound echo signal segment (see, e.g., FIG. 2). With reference to FIG. 2, in an exemplary embodiment a bracketed segment of a portion of an ultrasound echo signal is digitized and provided to both the Low Band IB Processor (associated with a relatively low sub-band of an operating frequency range of system 100) and the High Band IB Processor (associated with a relatively high sub-band of the operation frequency range of system 100) of the characterization application 132 to render corresponding Low and High Band IB parameter values for the echo signal segment. Turning briefly to FIG. 3 showing an exemplary gray-scale IVUS image, in an exemplary embodiment, the system 100 correlates a time of receipt of the bracketed echo signal segment with a range (distance from a transducer element) along a scan line (the dotted horizontal line) in a field of view of an ultrasound probe.

The spectral resolution-enhanced IB parameter value sets extracted from the echo information rendered by the catheter 120 for a same echo signal segment are evaluated and applied to tissue characterization criteria that incorporate the frequency response signatures associated with particular types of plaque tissue. The IB parameter values are potentially applied in association with other extracted parameters rendered by other signal processors, to the characterization criteria incorporated in the characterization application 132, to render a tissue characterization for a point within a field of view of the ultrasound probe corresponding to an echo signal segment from which the IB parameter values were derived.

It is noted that while a tissue characterization is based on a single echo signal segment in the illustrative example described above, in alternative embodiments multiple echo signal segments and/or IB parameter values are combined with temporal/spatial neighbors to render values that exhibit improved signal/noise ratios. Thus, multiple echo signal segments from adjacent scan lines or repeated firings on a same scan line can be combined and presented to the Low and High Band IB processors. Also, multiple IB parameter values corresponding to the signal segments are potentially combined. In either case, the combination potentially improves the overall signal/noise ratio.

A data storage 134 stores the tissue characterizations rendered by the characterization application 132 based upon parametric information generated from the Low and High Band IB processors (and potentially other extracted parametric data) to the characterization criteria. The data storage 134 is, by way of example, any of a variety of data storage devices, including RAM, cache memory, flash memory, magnetic disks, optical disks, removable disks, SCSI disks, IDE hard drives, tape drives, optically encoded information discs (e.g., DVD) and all other types of data storage devices (and combinations thereof, such as RAID devices) generally known to those skilled in the art.

In the illustrative example, the tissue characterization application 132 exists as a single application comprising multiple integrated backscatter parameter value processor components corresponding to multiple frequency sub-bands for which IB parameter values are calculated for each ultrasound echo segment. However, in other embodiments, the characterization application 132 comprises multiple applications/components executed on one or more computing devices (including multiple processor systems as well as groups of networked computers). Thus, the number and location of the components depicted in FIG. 1 are not intended to limit the present invention, and are merely provided to illustrate the environment in which an exemplary system operates. Thus, for example, a computing device having a plurality of data storage devices and/or a remotely located characterization application (either in part or in whole) is within the spirit and scope of the present invention.

Figure 6A:
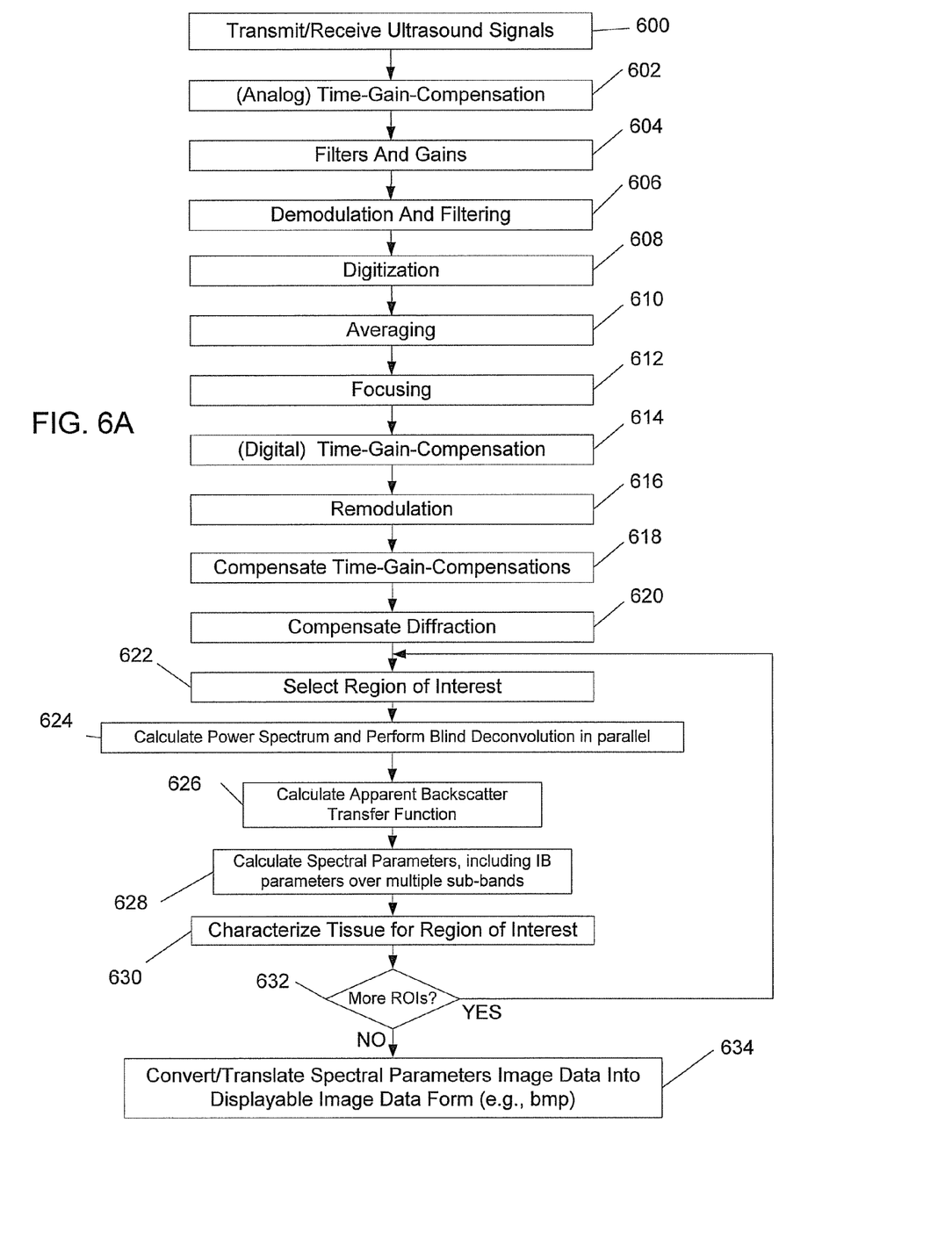
FIGS. 6a and 6b each describes a set of processing stages for rendering parametric information for characterizing plaque tissue.
Figure 6B:
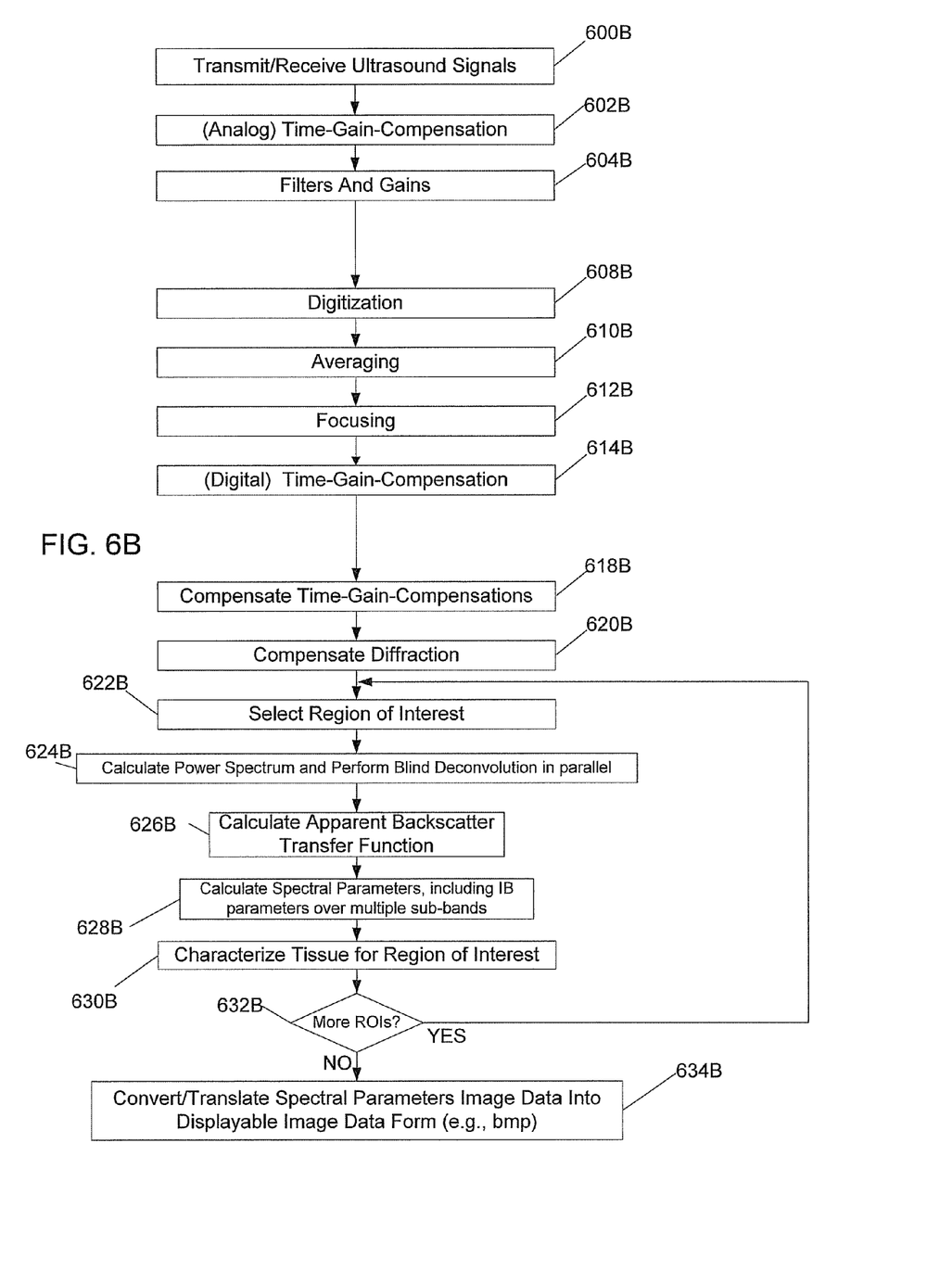

FIGS. 6a and 6b each describes an exemplary set of processing stages for rendering parametric information for characterizing plaque tissue in accordance with different raw IVUS signal processing architectures. Referring to FIG. 6a, a set of steps are summarized for processing data that is initially provided in the data domain (i.e., as baseband data)—requiring significantly less signal data to be stored since the digitized raw RF signal is converted to data components rather than preserving a digitized version of the time domain RF signal. In the exemplary embodiment, wherein the split-spectrum analysis is performed in the RF domain, "remodulation" of the data signal (back to the RF domain) is performed in preparation for generation of the ABSTF for the selected ultrasound echo signal segments.

During step 600 an ultrasound probe transmits ultrasound pulses and receives ultrasound echo signals from backscatters within the field of view defined by a set of scan lines. The received analog echo signals are passed to a patient interface module wherein, during step 602, the analog signals are time-gain compensated via amplifier circuitry to accommodate the inherent drop off of reflected energy as a function of distance from the ultrasound probe. Next, during step 604 the compensated analog signal is filtered and amplified in preparation for extracting a data signal.

Thereafter, during step 606 data is extracted from the compensated analog echo signal by a filter and gain stage. The resulting analog data signal is thereafter digitized during step 608. In an exemplary embodiment a 16 bit signed digital value is stored for each sample.

In an exemplary embodiment, an averaging operation is performed on the digitized data during step 610 to improve a signal to noise ratio of the digitized data. Next, during step 612 a focusing operation is performed to render additional echo image data. Focusing (i.e., beamforming) combines signals from a neighborhood of array elements in order to improve sensitivity. A similar process can be performed with consecutive transmissions when using an ultrasonic probe that is comprised of a single element. Thus, while a signal segment is referred to herein in singular form, the ultrasound echo signal segment referred to herein is potentially a sum of multiple spatial or temporal echo signals received by the IVUS system. It is furthermore noted that for a given region of interest, multiple ABSTF functions/curves associated with points on a scan line and neighboring scan lines are combined to render an ABSTF for a given region of interest.

During step 614 additional time-gain compensation is applied to the focused digitized data signal. Thereafter, during step 616, the data signal is remodulated. Remodulation transforms data-domain data back to RF-domain data which is utilized by the Low and High Band IB processors.

During step 618 additional compensation operations are performed on the time-gain compensated time-domain signal.

During step 620 additional operations are performed on the modulated data to compensate for diffraction effects on the ultrasound echo signal.

Thereafter an echo signal segment corresponding to a region of interest in the ultrasound probe's field of view is selected in step 622. Selection of an echo signal segment, in an exemplary embodiment, comprises selecting an echo signal segment for multiple scan lines and points within a scan line to improve signal/noise characteristics. In an exemplary embodiment, the segments are independently processed through ABSTF and IB parameter calculations. The IB parameter calculations for each echo signal segment are averaged prior to application of characterization criteria during step 630 described herein below.

The power spectrum of the region of interest of the compensated time-domain remodulated signal is calculated in parallel with a blind deconvolution operation to calculate the system transfer function for the region of interest during step 624. The ABSTF curve (See FIG. 4) is then calculated in step 626.

Based upon the selection of the region of interest during step 622, during step 628 spectrally distinct parameter values (e.g., IB values) are calculated for each of at least two sub-bands of a device's operation frequency band in accordance with the above-described IB parameter generation operation. Thereafter, the spectrally resolved IB parameter values for each echo signal segment for potentially multiple echo signal segments processed for a region of interest are submitted to tissue characterization criteria for classifying the tissue during step 630.

During step 630, the spectrally resolved IB parameters are applied in a variety of ways to tissue characterization criteria. In an exemplary embodiment, the Low Band IB parameter value corresponds to the IB parameter value from the low end of the system bandwidth (e.g., −20 dB level) to the mid-band, the High Band IB parameter value corresponds to the IB parameter value from the mid-band to the high end of the system bandwidth, and at least one IB parameter value comparison provided to the characterization criteria includes a difference between the High Band IB parameter value and the Low Band IB parameter value. The difference is a signed value representing the relative magnitudes of the High and Low IB parameter values. In yet another embodiment, the at least one IB parameter value comparison provided to the characterization criteria includes a ratio based upon the High Band IB parameter value and the Low Band IB parameter value.

As noted above, the IB parameter values for multiple echo signal segments associated with a region of interest are averaged spatially and/or temporally during step 626 or 628 to improve signal/noise characteristics. The spectrally resolved IB parameter values for each of the multiple echo signal segments are combined (e.g., averaged) prior to applying the averaged spectrally resolved signals to the characterizing criteria during step 630 to characterize the tissue in the current region of interest.

Next, at step 632 if additional regions of interest are available, then control returns to step 622. Otherwise, control passes to step 634 wherein the system applies previously determined characterizations for regions of interest to render displayable image data.

Briefly referring to FIG. 6B, the steps (with a B appended to reference numbers previously described with reference to FIG. 6A) in a time domain-based system are similar to the correspondingly identified steps in FIG. 6A. However, the time domain system that operates upon the analog signal does not perform the Demodulation and Filtering step 606 and the Remodulation step 616 that are needed in the baseband-based system represented in FIG. 6A.

Figure 7:
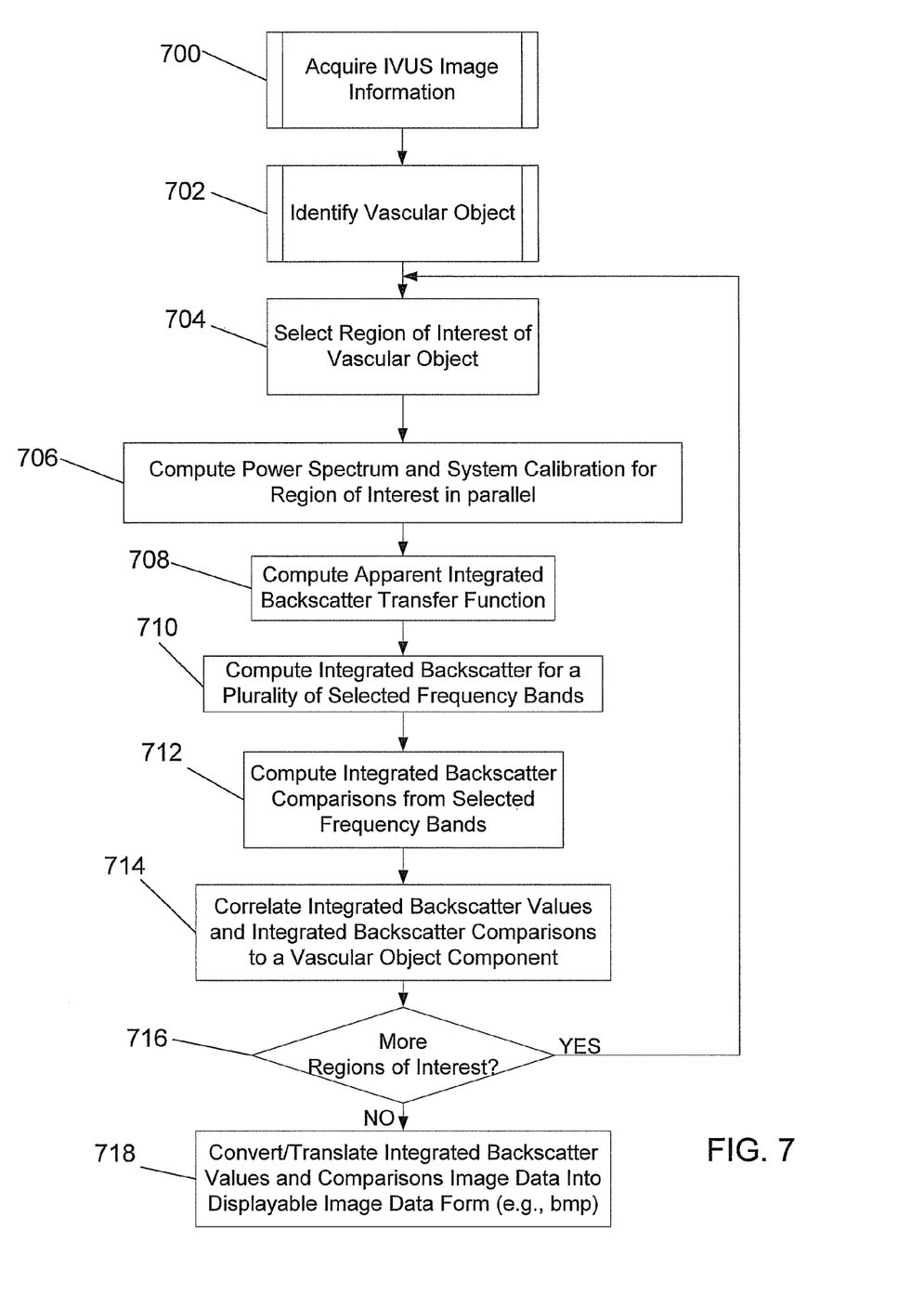
FIG. 7 is a flowchart summarizing an exemplary set of steps for generating integrated backscatter information to generate plaque tissue characterization data in accordance with an illustrative embodiment of the present invention.

FIG. 7 is a flowchart summarizing an exemplary set of steps for generating integrated backscatter information to generate plaque tissue characterization data in accordance with an illustrative embodiment of the present invention. During step 700 the tissue characterization application acquires raw IVUS image data. Next, at step 702 a vascular object is identified by a user. Thereafter, at step 704 the user selects a region of interest within an imaging probes' present field of view.

At step 706, the system independently computes in parallel the power spectrum for an echo signal segment and the system calibration information for the selected region of interest. Such calibration information includes, but is not limited to the point spread function and system transfer function (e.g., blind deconvolution).

Thereafter, at steps 708 and 710 the system calculates the ABSTF (708) and IB parameters at multiple sub-bands (710) for the selected region of interest. During step 712, in an exemplary embodiment a low and high sub-band IB are compared to render a signed difference signal (as opposed to an unsigned magnitude value) that potentially aids correlating a signal's parameter value with a particular tissue characterization.

Next, during step 714 the values computed during steps 710 and 712 are applied to characterization criteria to render a tissue characterization. If additional regions of interest exist, then control passes from step 716 back to step 704. Otherwise, at step 718 the designated characterizations for the various regions of interest are combined into a single displayed image according to the assigned tissue characterizations.

The IB parameters calculated within two or more bands of a larger spectral band, by a system embodying the aforementioned ultrasound echo parameterization scheme, are used as input to a tissue characterization application that utilizes parametric data provided by potentially many sources to render a tissue type corresponding to an ultrasound echo segment. An example of such system is described, by way of example, in Nair et al., U.S. application Ser. No. 11/689,327.

The tissue characterization output of the above-described system is thereafter used, by way of example, to provide input to a system for classifying vascular plaque lesions wherein a classification criterion is applied by a plaque classification application to at least one graphical image of a cross-sectional slice of a vessel to render an overall plaque classification for the slice or set of slices, covering a 3D volume. Such system is described, by way of example, in Margolis et al., U.S. application Ser. No. 11/689,963.

It is noted that while the illustrative embodiment discloses the use of two frequency bands, in alternative embodiments more bands are used. Furthermore, the multiple bands may overlap or have band gaps between them.

Systems and their associated components have been described herein above with reference to exemplary embodiments of the invention including their structures and techniques. It is noted that the present invention is implemented in computer hardware, firmware, and software in the form of computer-readable media including computer-executable instructions for carrying out the described functionality. In view of the many possible embodiments to which the principles of this invention may be applied, it should be recognized that the embodiments described herein with respect to the drawing figures are meant to be illustrative only and should not be taken as limiting the scope of invention. Therefore, the invention as described herein contemplates all such embodiments as may come within the scope of the following claims and equivalents thereof.

What is claimed is:

1. A method for characterizing plaque tissue in accordance with received intravascular ultrasound echo segments, the method comprising:
   collecting analog intravascular ultrasound echo signals from tissue in a region of interest in a portion of an imaged body;
   computing, from RF-domain ultrasound echo signal segment data derived from the analog ultrasound echo signals, spectrally resolved information over an operating frequency range resulted from a single transmitted frequency including:
   a power spectrum by performing spectral analysis, and
   a system transfer function;
   determining, in each of at least a first sub-band and a second sub-band within the operating frequency range, an integrated backscatter parameter from the power spectrum and system transfer function;
   comparing integrated backscatter values from at least the first sub-band and the second sub-band to obtain at least one integrated backscatter comparison parameter value;
   applying the at least one integrated backscatter comparison parameter value to at least one tissue characterization criterion for rendering a plaque tissue characterization of the tissue in the region of interest; and
   generating an image of the region of interest in accordance with the plaque tissue characterization of the tissue in the region of interest.

2. The method of claim 1 further comprising applying an integrated backscatter parameter value from the first sub-band directly to the at least one tissue characterization criterion.

3. The method of claim 2 further comprising applying an integrated backscatter parameter value from the second sub-band directly to the at least one tissue characterization criterion.

4. The method of claim 1 wherein the at least one integrated backscatter comparison parameter value is based upon a difference between integrated backscatter parameter values for the first sub-band and the second sub-band.

5. The method of claim 4 wherein the difference is a signed value representing the relative magnitudes of the integrated backscatter parameter values for the first sub-band and the second sub-band.

6. The method of claim 1 wherein the at least one integrated backscatter comparison parameter value is based upon a ratio of integrated backscatter parameter values for the first sub-band and the second sub-band.

7. The method of claim 1 wherein the determining step comprises computing an apparent backscatter transfer function (ABSTF) over at least the first sub-band and the second sub-band.

8. The method of claim 1 wherein the computing step comprises computing the system transfer function by performing blind deconvolution.

9. The method of claim 1 wherein the at least one tissue characterization criterion utilizes the backscatter comparison parameter to identify fibro-fatty plaque tissue.

10. The method of claim 1 wherein the at least one tissue characterization criterion utilizes the backscatter comparison parameter to identify necrotic core plaque tissue.

11. A non-transitory computer-readable medium including computer-executable instructions for characterizing plaque tissue in accordance with received intravascular ultrasound echo segments, the computer-executable instructions facilitating performing, on analog ultrasound echo signals collected from tissue in a region of interest in a portion of an imaged body, the steps of:

computing, from RF-domain ultrasound echo signal segment data derived from the analog ultrasound echo signals, spectrally resolved information over an operating frequency range including:

a power spectrum by performing spectral analysis, and a system transfer function;

determining, in each of at least a first sub-band and a second sub-band within the operating frequency range, an integrated backscatter parameter from the power spectrum and system transfer function;

comparing integrated backscatter values from at least the first sub-band and the second sub-band to obtain at least one integrated backscatter comparison parameter value; and     applying the at least one integrated backscatter comparison parameter value to at least one tissue characterization criterion for rendering a plaque tissue characterization of the tissue in the region of interest; and     generating an image of the region of interest in accordance with the plaque tissue characterization of the tissue in the region of interest.

12. The computer-readable medium of claim 11 further comprising computer-executable instructions for applying an integrated backscatter parameter value from the first sub-band directly to the at least one tissue characterization criterion.

13. The computer-readable medium of claim 12 further comprising computer-executable instructions for applying an integrated backscatter parameter value from the second sub-band directly to the at least one tissue characterization criterion.

14. The computer-readable medium of claim 11 wherein the at least one integrated backscatter comparison parameter value is based upon a difference between integrated backscatter parameter values for the first sub-band and the second sub-band.

15. The computer-readable medium of claim 14 wherein the difference is a signed value representing the relative magnitudes of the integrated backscatter parameter values for the first sub-band and the second sub-band.

16. The computer-readable medium of claim 11 wherein the at least one integrated backscatter comparison parameter value is based upon a ratio of integrated backscatter parameter values for the first sub-band and the second sub-band.

17. The computer-readable medium of claim 11 wherein the determining step comprises computing an apparent backscatter transfer function (ABSTF) over at least the first sub-band and the second sub-band.

18. The computer-readable medium of claim 11 wherein the computing step comprises computing the system transfer function by performing blind deconvolution.

19. The computer-readable medium of claim 11 wherein the at least one tissue characterization criterion utilizes the backscatter comparison parameter to identify fibro-fatty plaque tissue.

20. The computer-readable medium of claim 11 wherein the at least one tissue characterization criterion utilizes the backscatter comparison parameter to identify necrotic core plaque tissue.

* * * * *